United States Patent [19]
Chen

[11] Patent Number: 5,907,397
[45] Date of Patent: May 25, 1999

[54] METHOD OF INSPECTING A DEFECT ON A TRANSLUCID FILM

[75] Inventor: Anchor Chen, Pingtung, Taiwan

[73] Assignee: United Semiconductor Corp., Hsinchu, Taiwan

[21] Appl. No.: 09/045,325

[22] Filed: Mar. 20, 1998

[51] Int. Cl.$^6$ .................................................. G01N 21/00
[52] U.S. Cl. .................... 356/237.2; 356/36; 356/237.4; 356/382
[58] Field of Search .................. 356/237.2, 36, 356/382, 372, 237.4

[56] References Cited

U.S. PATENT DOCUMENTS

| | | | |
|---|---|---|---|
| 5,569,342 | 10/1996 | Gould et al. | 356/237.2 |
| 5,576,831 | 11/1996 | Nikoondrud et al. | 356/237.2 |
| 5,742,386 | 4/1998 | Nose et al. | 356/237.2 |

*Primary Examiner*—Robert Kim
*Assistant Examiner*—Reginald A. Ratliff
*Attorney, Agent, or Firm*—Thomas, Kayden, Horstemeyer & Risley, L.L.P.

[57] ABSTRACT

A method of the invention for inspecting a defect on a translucid film is provided. The method includes an anti-reflective coating (ARC) layer over the translucid film. The anti-reflective coating (ARC) layer prevents inspecting light from penetrating through the ARC layer and reduces the amount of inspecting light refracting through the translucid film. The inspection is performed by generating an inspecting light with a predetermined angle radiating on the ARC layer. The reflecting light message from different regions of the anti-reflective coating (ARC) layer are separately collected. The reflecting light messages are compared die to die to calculate an inspecting result.

16 Claims, 1 Drawing Sheet

METHOD OF INSPECTING A DEFECT ON A TRANSLUCID FILM

BACKGROUND OF THE INVENTION

1. Field of the Invention

The invention relates in general to the method of inspecting a defect on a translucid film, and more particularly to the method of inspecting a defect on a translucid film by adding an anti-reflective coating (ARC) on the translucid film.

2. Description of the Related Art

In the semiconductor process, after forming an translucid layer, for example, an oxide layer, on a semiconductor substrate by deposition, there is usually a following polishing step to flatten the surface of the translucid layer. The preferred polishing is chemical mechanical polishing (CMP). After polishing, the engineers inspect the quality of the insulating layer by several methods. Currently, the preferred inspecting method includes Tenco particle inspection using the American Tenco AIT-type machine. Generally speaking, the insulating layer can be considered a translucid layer. When an incident light radiates on the surface of the insulating layer, it usually generates both refraction and reflection. The reflective light reflects back from the surface of the insulating layer and the refractive light penetrates the insulating layer. Therefore, engineers usually term the insulating layer the translucid layer.

A conventional method to inspect a defect on a translucid film is Tenco particle inspection. First, an incident light is provided, for example, laser light with a predetermined angle. The incident light radiates on the surface of the translucid layer to inspect a defect particle on the translucid layer. The predetermined angle is determined to make total reflection on the translucid layer. The reflective light reflects from the translucid layer and is collected by Tenco inspectors. The reflective lights reflecting from different regions of the translucid layer, for example, different dies, have different light messages.

FIG. 1 showing a conventional method of inspecting a defect on a translucid film. First, a semiconductor substrate 10 is provided. A translucid layer 11, for example, an oxide layer, is formed on the semiconductor substrate 10 by deposition. Polishing the translucid layer 11 is performed to flatten the surface of the translucid layer 11 using chemical mechanical polishing (CMP). After polishing, defect particles 12 are formed and dishes 14 are formed because of dishing effects. Then an inspecting step is performed. A laser light with a predetermined angle radiates on the translucid layer 11. There are reflections from different regions of the translucid layer 11. As shown in FIG. 1, light 13A totally reflects from the translucid layer 11 and light 13B which radiates on sidewall of the dish 14 partially reflects and partially refracts. Partial light 13B refracts through the translucid layer 11 and partial light 13B reflects from the surface of the translucid layer 11. Light 13C scatters because of the defect particle 12.

At the beginning, the incident light with the predetermined angle satisfies total reflection conditions. The predetermined angle is determined satisfying the total reflection angle. When the incident light radiates on the dish 14 which is formed because of dishing effect, the predetermined angle on the dish 14 is no longer the total reflection angle. Therefore, the incident light radiating on the dish 14 partially reflects and partially refracts. If the incident light partially refracts through the translucid layer 11, the partially refracting light then reflects on the semiconductor substrate 10. The reflecting light from the semiconductor substrate 10 disturbs the original incident light to generate variable light intensity. The variable light intensity (color variation) affects inspection, reducing the accuracy of inspection results.

SUMMARY OF THE INVENTION

It is an object of the invention to provide a method of inspecting a defect on a translucid film by adding an anti-reflective coating (ARC) layer on the translucid film to prevent inspecting light from penetrating through the anti-reflective coating (ARC) layer.

It is an object of the invention to provide a method of inspecting a defect on a translucid film that reduces refraction of the inspecting light through the translucid film.

It is another object of the invention to provide a method of inspecting a defect on a translucid film to reduce the color variation and to improve the inspection results.

A method of fabricating a trench isolation comprises the following steps. First a semiconductor substrate is provided. The semiconductor substrate at least includes a first die region and a second die region. A translucid layer is formed on the semiconductor substrate. The translucid layer is polished and a defect particle is then formed on the surface of the translucid layer in the first die region. An ARC layer is formed on the translucid layer and the defect particle. Next, an inspector is provided to radiate an inspecting light with a predetermined angle on the ARC layer. The reflected light message from the first die region and the second die region are separately collected. The reflecting light message is compared die to die to calculate an inspection result.

BRIEF DESCRIPTION OF THE DRAWINGS

Other objects, features, and advantages of the invention will become apparent from the following detailed description of the preferred but non-limiting embodiments. The description is made with reference to the accompanying drawings in which.

DESCRIPTION OF THE PREFERRED EMBODIMENT

The method of the invention is to inspect a defect on a translucid film by adding an anti-reflective coating (ARC) layer on the translucid film. The anti-reflective coating (ARC) layer prevents the inspecting light from penetrating through the ARC layer and reduces refraction of the inspecting light through the translucid film.

Figure 1:
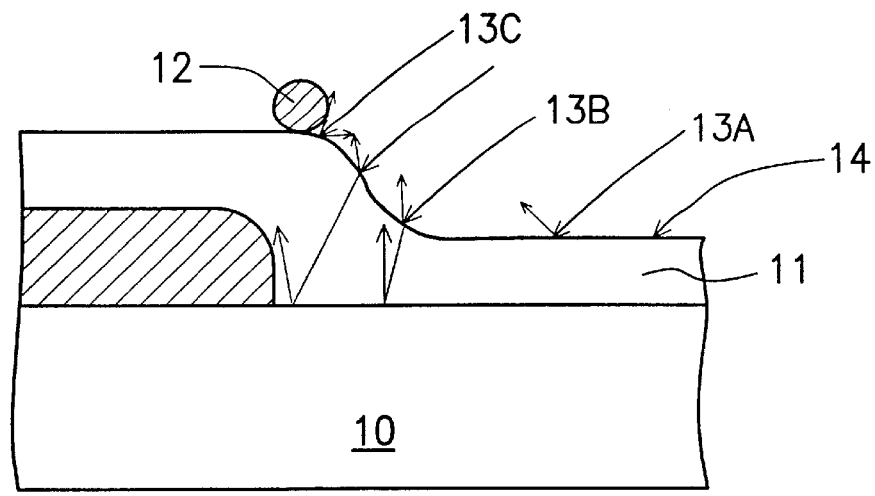
FIG. 1 is a cross-sectional view showing a conventional method of inspecting a defect on a translucid film.
Figure 2:
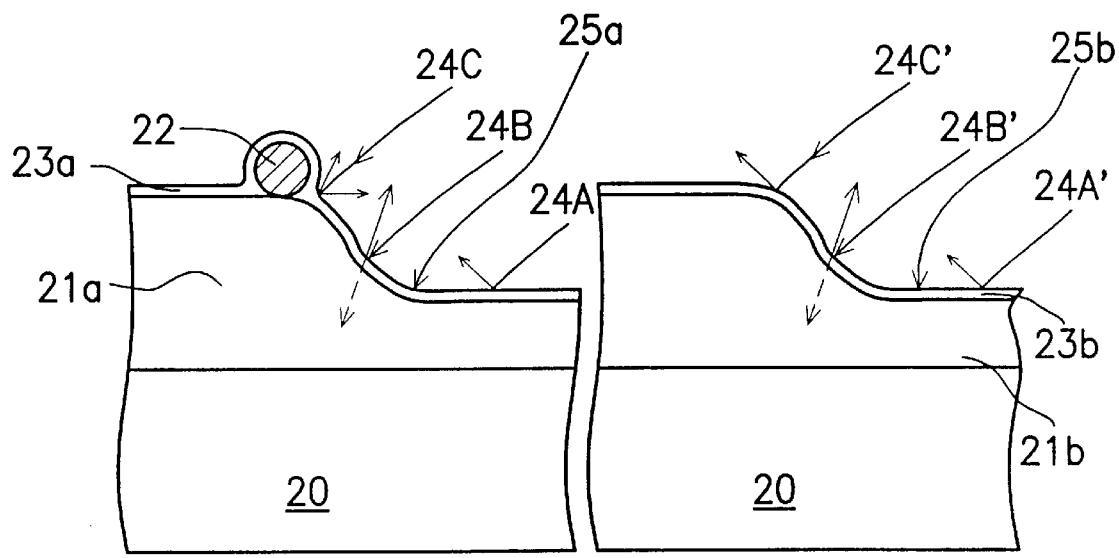
FIG. 2 is a cross-sectional view showing a method of inspecting a defect on a translucid film according to the invention.

FIG. 2 is a cross-sectional view showing a method of inspecting a defect on a translucid film according to the invention. First, a semiconductor substrate 20 is provided including a first die region and a second die region. Translucid layers 21a and 21b are formed, for example, silicon oxide layers, on the semiconductor substrate 20 by deposition. The translucid layer 21a is formed on the first die region and the translucid layer 21b is formed on the second die region. Polishing is performed to flatten the translucid layers 21a and 21b. The preferred polishing is chemical mechanical polishing (CMP). Defect particles 22 and dishes 25a and 25b formed after polishing due to the dishing effects, on the surface of the translucid layers 21a and 21b. Then anti-reflective coating (ARC) layers 23a and 23b are formed separately on the translucid layers 21a and 21b. The ARC layers 23a and 23b include ARC materials, organic matters removed and inorganic matters remaining, titanium nitride or metal. The ARC layers 23a and 23b are used to reduce the light strength of inspecting light refracting through the translucid layers 21a and 21b. Namely, the ARC layers 23a and 23b are used to prevent the inspecting light from penetrating through the ARC layers 23a and 23b. There is almost no refracting light through the translucid layers 21a and 21b and the inspecting light partially reflects from the ARC layers 23a and 23b.

Next, an inspector is provided to inspect the surface of the translucid layers 21a and 21b. The preferred inspector is Tenco AIT particle inspector. A laser light with a predetermined angle from the inspector radiates onto the translucid layers 21a and 21b. The laser light includes multi-frequency laser light for reducing interference effect. The predetermined angle is defined as the acute angle between the laser light and the semiconductor substrate 20. The preferred predetermined angle is about 0–45 degrees to satisfy the condition of total reflection. The incident laser lights include light 24A–24C and 24A'–24C' with the same incident angle and every light reflects from different regions of the translucid layers 21a and 21b. As shown in FIG. 2, light 24A totally reflects from the ARC layer 23a and light 24A' totally reflects from the ARC layer 23b. Light 24B which radiates on sidewall of the dish 25a partially reflects and partially refracts. Light 24B' which radiates on sidewall of the dish 25b partially reflects and partially refracts, too. The refracting lights of inspecting light 24B and 24B' are almost absorbed by the ARC layers 23a and 23b. There is almost no light refracting through the translucid layers 21a and 21b, as shown by the dotted line in FIG. 2. Therefore, reflected light from the semiconductor substrate 20 decreases and the color variation reduced. Light 24C radiating on the defect particle 22 scatters. Light 24C' radiating on the corresponding place of the defect particle 22 doesn't scatter because of no defect particle.

Next, all of the reflecting light from the ARC layer 23a and the reflecting light from the ARC layer 23b are collected. The reflecting light messages from the ARC layer 23a and the ARC layer 23b are compared die to die to calculate an inspecting result.

The method of the invention to inspect a defect on a translucid film has the following characteristics:

1. The ARC layers 23a and 23b of the invention are to reduce the inspecting light refracting through the translucid layers 21a and 21b and to reduce the degradation of inspection of dishes 25a and 25b. The probabilities of misjudgement of the inspection are therefore decreased.

2. According to the invention, the inspecting light refracting through the translucid layers 21a and 21b and the reflecting light from the semiconductor substrate 20 are reduced to avoid the interference effect and the color radiation. The inspection result is then improved.

While the invention has been described by way of example and in terms of preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications, similar arrangements and procedures.

What is claimed is:

1. A method of inspecting a defect on a translucid film, comprising the steps of:

providing a semiconductor substrate;

forming a translucid layer on the semiconductor substrate;

polishing the translucid layer and forming a defect particle on the surface of the translucid layer;

forming a buffer layer on the translucid layer and the defect particle, for preventing light from penetrating through the buffer layer;

providing an inspector to generate an inspecting light with a predetermined angle radiating on the buffer layer; and collecting and calculating the reflecting light message from the buffer layer to calculate an inspection result.

2. A method as claimed in claim 1, wherein the translucid layer is silicon oxide.

3. A method as claimed in claim 1, wherein the buffer layer includes anti-reflective coating (ARC) materials.

4. A method as claimed in claim 1, wherein the buffer layer includes inorganic matters.

5. A method as claimed in claim 1, wherein the buffer layer includes titanium nitride.

6. A method as claimed in claim 1, wherein the buffer layer includes metal.

7. A method as claimed in claim 1, wherein the inspector is Tenco AIT particle inspector.

8. A method as claimed in claim 1, wherein the predetermined angle is defined as the acute angle between the inspecting light and the semiconductor substrate, and the predetermined angle is about 0–45 degrees.

9. A method of inspecting a defect on a translucid film, comprising the steps of:

providing a semiconductor substrate, the semiconductor substrate at least including a first die region and a second die region;

forming a translucid layer on the semiconductor substrate;

polishing the translucid layer and forming a defect particle on the surface of the translucid layer on the first die region;

forming a buffer layer on the translucid layer and the defect particle, for preventing light from penetrating through the buffer layer;

providing an inspector to generate an inspecting light with a predetermined angle radiating on the buffer layer; and collecting separately the reflecting light message from the first die region and the second die region and comparing the reflecting light message die to die to calculate an inspecting result.

10. A method as claimed in claim 9, wherein the translucid layer is silicon oxide.

11. A method as claimed in claim 9, wherein the buffer layer includes anti-reflective coating (ARC) materials.

12. A method as claimed in claim 9, wherein the buffer layer includes inorganic matters.

13. A method as claimed in claim 9, wherein the buffer layer includes titanium nitride.

14. A method as claimed in claim 9, wherein the buffer layer includes metal.

15. A method as claimed in claim 9, wherein the inspector is Tenco AIT particle inspector.

16. A method as claimed in claim 9, wherein the predetermined angle is defined as the acute angle between the inspecting light and the semiconductor substrate, and the predetermined angle is about 0–45 degrees.

* * * * *